(12) United States Patent
Ohara et al.

(10) Patent No.: US 6,335,449 B1
(45) Date of Patent: Jan. 1, 2002

(54) PROCESS FOR THE PREPARATION OF QUINOLINE DERIVATIVE AND INTERMEDIATE THEREFOR

(75) Inventors: Yoshio Ohara; Mikio Suzuki; Yoshinobu Yanagawa; Yasutaka Takada, all of Chiba (JP)

(73) Assignee: Nissan Chemical Industries, Ltd., Tokyo (JP)

(*) Notice: Subject to any disclaimer, the term of this patent is extended or adjusted under 35 U.S.C. 154(b) by 0 days.

(21) Appl. No.: 09/764,994

(22) PCT Filed: Jul. 22, 1999

(86) PCT No.: PCT/JP99/03923

§ 371 Date: Jan. 23, 2001

§ 102(e) Date: Jan. 23, 2001

(87) PCT Pub. No.: WO00/05213

PCT Pub. Date: Feb. 3, 2000

(30) Foreign Application Priority Data

Jul. 23, 1998 (JP) .............................. 10-207911

(51) Int. Cl.⁷ .................... C07D 215/04; C07D 215/12; C07D 215/18

(52) U.S. Cl. ................... 546/173; 546/174; 546/176; 546/180

(58) Field of Search ................... 546/173, 174, 546/176, 180

(56) References Cited

U.S. PATENT DOCUMENTS

| | | | |
|---|---|---|---|
| 5,011,930 A | 4/1991 | Fujikawa et al. |
| 5,102,888 A | 4/1992 | Fujikawa et al. |
| 5,185,328 A | 2/1993 | Fukikawa et al. |
| 5,284,953 A | 2/1994 | Ohara et al. |
| 5,473,075 A | 12/1995 | Ohara et al. |
| 5,514,804 A | 5/1996 | Ohara et al. |
| 5,854,259 A | 12/1998 | Fujikawa et al. |
| 5,856,336 A | 1/1999 | Fujikawa et al. |
| 5,872,130 A | 2/1999 | Fujikawa et al. |
| 5,939,552 A | 8/1999 | Ikeda et al. |
| 6,162,798 A | 12/2000 | Saito et al. |

FOREIGN PATENT DOCUMENTS

| | | | |
|---|---|---|---|
| DE | 3905908 | * | 9/1990 |
| JP | 01279866 | * | 11/1989 |
| JP | 06329540 | * | 11/1994 |

OTHER PUBLICATIONS

U.S. application No. 09/436,789, filed Nov. 8, 1999, pending.*
U.S. application No. 09/743,810, filed Jan. 22, 2001, pending.*
U.S. application No. 09/764,994, filed Jan. 23, 2001, pending.*

* cited by examiner

Primary Examiner—D. Margaret Seaman
(74) Attorney, Agent, or Firm—Oblon, Spivak, McClelland, Maier & Neustadt, P.C.

(57) ABSTRACT

The present invention relates a process for producing the quinoline derivative (3) via the nitrile compound (1) obtained by reacting the aldehyde compound represented by formula (2) with diethyl cyanomethylphosphonate and its intermediate (1).

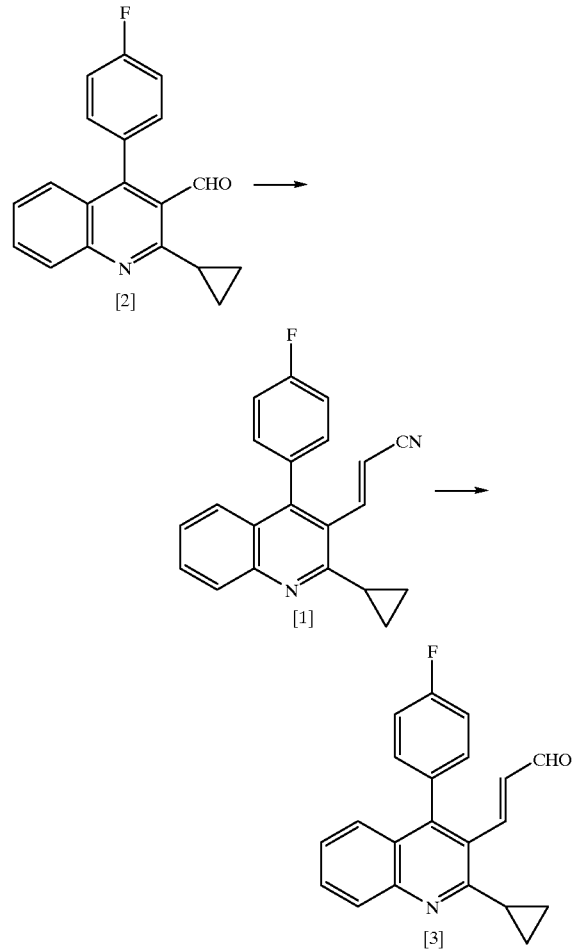

2 Claims, No Drawings

PROCESS FOR THE PREPARATION OF QUINOLINE DERIVATIVE AND INTERMEDIATE THEREFOR

INTERMEDIATE

This application is a 371 of PCT/GP99/03923, filed Jul. 22, 1999.

TECHNICAL FIELD

The present invention relates to a process for producing the quinoline derivative represented by formula (3) which can be a useful intermediate of cholesterol reducing agents (HMG-CoA reductase inhibitors)

[3]

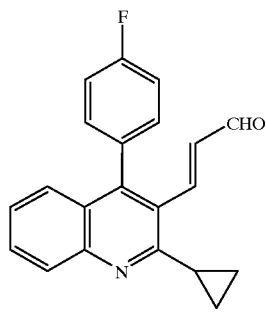

BACKGROUND ART

The quinoline compound represented by formula (4) is disclosed in JP-A-1-279866, EP-A-304063 and U.S. Pat. No. 5,011,930 as a useful cholesterol reducing agent (HMG-CoA reductase inhibitor).

[4]

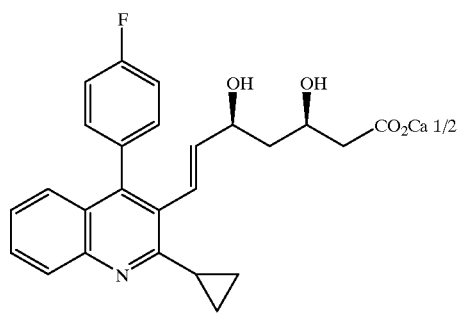

The quinoline compound represented by formula (4) is obtained in the above-mentioned patents as shown below by converting the aldehyde compound (2) into the $\alpha,\beta$-unsaturated carboxylic acid ester compound (5) followed by reduction into the alcohol compound (6) and oxidation into the desired quinoline compound (3). Though direct reduction of the $\alpha,\beta$-unsaturated carboxylic acid ester compound into the desired quinoline compound (3) would improve production efficiency, the problem is the difficulty of its control.

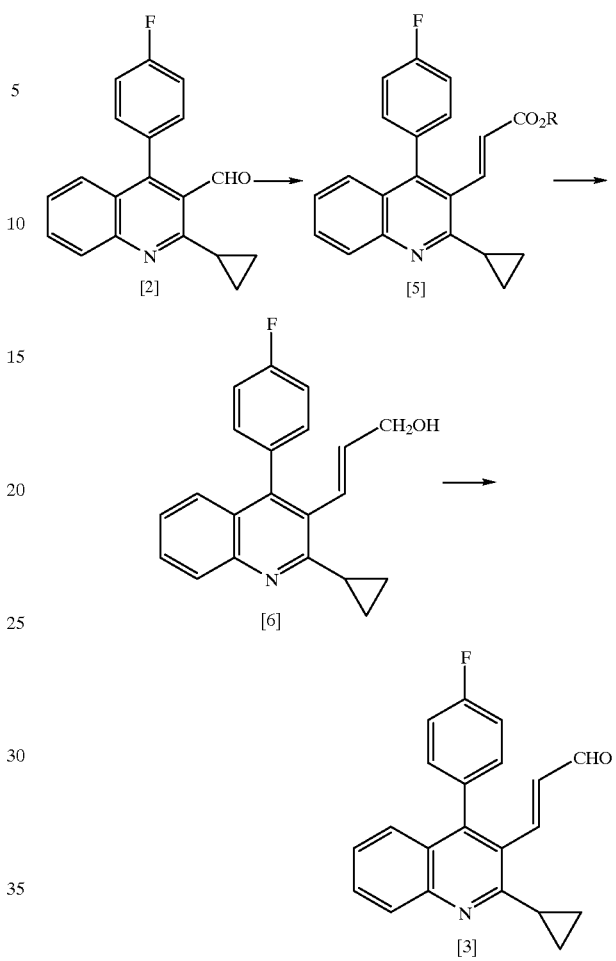

DISCLOSURE OF THE INVENTION

As a result of their extensive research to solve the above-mentioned problem, the present inventors found one-step preparation of the desired quinoline compound (3) via the nitrile compound (1) obtained by reacting the aldehyde compound (2) with diethyl cyanomethylphosphonate.

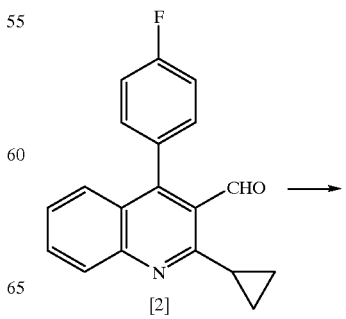

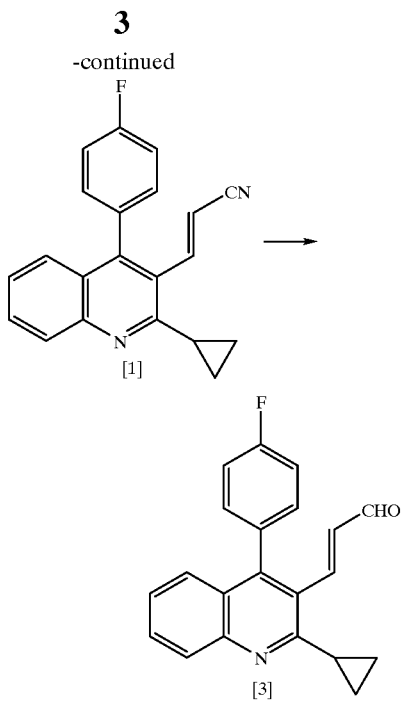

Namely, the present invention relates to a process for producing the quinoline derivative (3) via the nitrile compound (1) obtained by reacting the aldehyde compound represented by formula (2) with diethyl cyanomethylphosphonate and its intermediate (1).

One-step preparation of the desired quinoline compound (3) can be attained via the nitrile compound (formula (1)) obtained by reacting the aldehyde compound represented by formula (2) with diethyl cyanomethylphosphonate.

BEST MODE FOR CARRYING OUT THE INVENTION

Now, the process of the present invention will be described.

Preparation of Nitrile Compound (1)

As the solvent used in the reaction, an aromatic hydrocarbon such as toluene or xylene, an ethereal solvent such as tetrahydrofuran or dioxane or a halogenated solvent such as dichloroethane or o-dichlorobenzene may be mentioned.

From 0.5 to 5 times as many moles, preferably from 0.9 to 1.5 times as many moles, of diethyl cyanomethylphosphonate is used.

A base such as sodium hydride, sodium hydroxide, potassium hydride, sodium methoxide, sodium ethoxide, potassium t-butoxide or potassium carbonate may be used in an amount of from 0.5 to 10 times as many moles, depending on the solvent and the type of the base. A phase transfer catalyst such as Aliquat 336 may be used optionally, for example, when toluene as the solvent is combined with (aqueous) sodium hydroxide as the base.

The reaction temperature is within the range of from −20 to 80° C., preferably within the range of from 20 to 40° C.

Preparation of Quinoline Derivative (3)

Use of diisobutylaluminum hydride as a reducing agent and an aromatic hydrocarbon such as toluene or xylene as the solvent in the reaction gives good results. Diisobutylaluminum hydride is used in an amount of from 0.5 to 5 times as many moles, preferably from 0.9 to 1.5 times as many moles, and the reaction temperature is within the range of from −50 to 50° C., preferably within the range of from −30 to 5° C. Reduction with Raney nickel in formic acid as the solvent is also available.

EXAMPLE

Now, the present invention will be described in further details with reference to Examples. However, the present invention is by no means restricted to these specific Examples.

Preparation of Nitrile Compound (1)

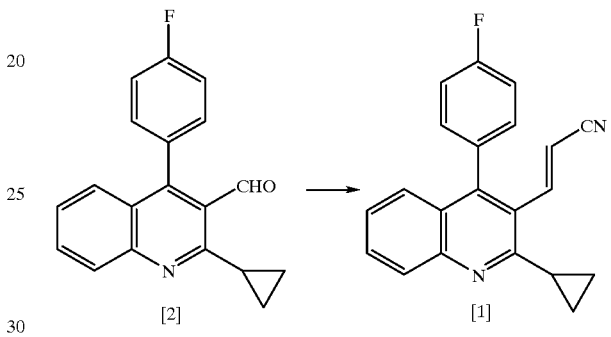

To a solution of 199 g (683 mmol) of 2-cyclopropyl-4-(4-fluorophenyl)quinoline-3-carboaldehyde in 960 g of toluene, 136 g (765 mmol, 1.1 eq) of diethyl cyanomethylphosphonate and 5.5 g (13.6 mmol, 0.02 eq) of Aliquat 336 were added.

400 g of 20% aqueous sodium hydroxide was added dropwise over 0.5–1 hour with stirring while the inner temperature was maintained at 25–35° C., and the reaction solution was stirred at the same temperature for 1 hour.

After completion of the reaction, 200 g of water was added, and the mixture was stirred for 30 minutes and allowed to separate. The resulting organic layer was washed with 400 ml of 10% aqueous sodium hydroxide, combined with 400 ml of saturated aqueous sodium chloride, adjusted to pH 7 with 1N aqueous hydrochloric acid and allowed to separate. After addition of 50 g of sodium sulfate, the resulting organic layer was stirred for 1 hour, then stirred for another 30 minutes together with 5 g of activated carbon and 20 g of silica gel and filtered through a celite-layered funnel.

The solvent was distilled off the filtrate under reduced pressure until the residual amount became about 400 g, and the precipitated crystals were melted in situ by heating and refluxed together with 580 g of hexane under heating for 30 minutes, then cooled to 5° C. and stirred at the same temperature for 2 hours. The precipitated crystals were collected by filtration, washed with toluene-hexane (1:5, w/w) and with hexane and dried to give 189 g of 3-{2-cyclopropyl-4-(4-fluorophenyl)-3-quinolyl}prop-2-enenitrite in a 88% yield. m.p. 176–178° C.

Preparation of Quinoline Derivative (3)

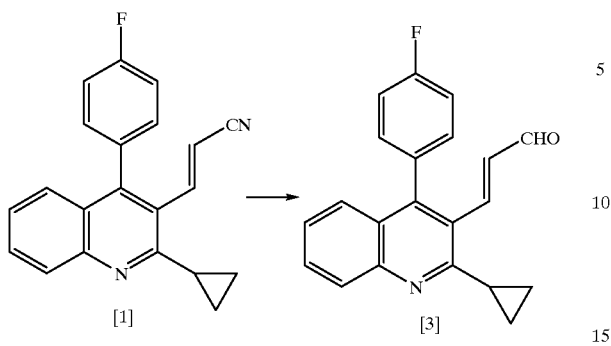

A solution of 181 g (576 mmol) of 3-{2-cyclopropyl-4-(4-fluorophenyl)-3-quinolyl}prop-2-enenitrite in 1812 ml of toluene was cooled to an inner temperature of −10° C. 650 ml of a 1.02 M toluene solution of diisobutylaluminum hydride (663 mmol, 1.15 eq) was added dropwise over 1 hour while the inner temperature was maintained at from −10 to −5° C., and the mixture was stirred at the same temperature for 1 hour.

After the reaction, 30.5 g of ethanol was added dropwise while the temperature was maintained at from −10 to −5° C., and the mixture was stirred at the same temperature for 30 minutes. 155 ml of 1 N hydrochloric acid was added dropwise while the temperature was maintained at 10° C. or below, and the mixture was stirred at the same temperature for 1 hour. Further, 9.06 ml of 35% hydrochloric acid was added dropwise while the temperature was maintained at the same temperature, and the mixture was stirred at an inner temperature of 25–30° C., and the resulting mixture was filtered through a celite-layered funnel.

After addition of 725 ml of 1 N hydrochloric acid, the filtrate was stirred for 30 minutes and allowed to separate. The organic layer was washed with 360 ml of 1 N hydrochloric acid and with 545 ml of saturated aqueous sodium chloride. All the aqueous layers were combined and extracted with 725 ml of ethyl acetate again, and the extract was washed with 360 ml of saturated aqueous sodium chloride and combined with the above-mentioned organic layer. After addition of 1090 ml of water, the mixture was adjusted to pH 7 with saturated aqueous sodium hydrogen carbonate and washed with 1090 ml of water and 1090 ml of saturated aqueous sodium chloride.

The solvent was distilled away from the resulting solution under reduced pressure, and 360 g of cyclohexane and 720 g of n-hexane were added. The mixture was refluxed under heating for 30 minutes, then cooled to 0–5° C. and stirred at the same temperature for 2 hours. The precipitated crystals were collected by filtration, washed with cyclohexane-n-hexane (1:2, w/w) and n-hexane and dried to give 170 g of 3-(2-cyclopropyl-4-(4-fluorophenyl)-3-quinolyl)prop-2-enal in a 93% yield. m.p.: 146–147° C.

What is claimed is:

1. A nitrile compound represented by formula (1)

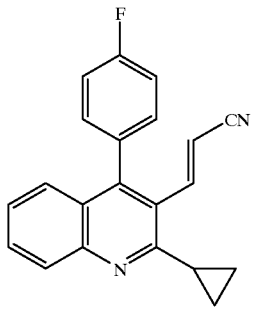

2. A process for producing the quinoline derivative (3) via the nitrile compound (1) obtained by reacting the aldehyde compound represented by formula (2) with diethyl cyanomethylphosphonate

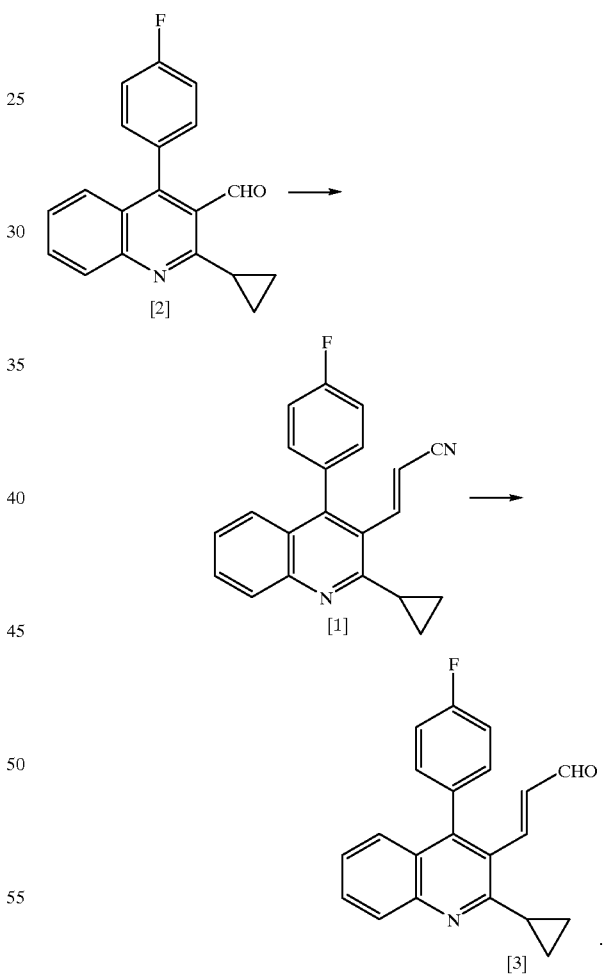

* * * * *

UNITED STATES PATENT AND TRADEMARK OFFICE
CERTIFICATE OF CORRECTION

PATENT NO.    : 6,335,449 B1
DATED         : January 1, 2002
INVENTOR(S)   : Yoshio Ohara et al.

It is certified that error appears in the above-identified patent and that said Letters Patent is hereby corrected as shown below:

<u>Column 4,</u>
Line 51, "with IN aqueous" should read -- with 1N aqueous --.
Line 67, "enenitrite" should read -- enenitrile --.

Signed and Sealed this

Third Day of December, 2002

JAMES E. ROGAN
*Director of the United States Patent and Trademark Office*